United States Patent [19]
del Valle et al.

[11] Patent Number: 5,094,961
[45] Date of Patent: Mar. 10, 1992

[54] ASPIRATION METHOD FOR HEMATOLOGY ANALYZING APPARATUS

[75] Inventors: Roberto del Valle; Santos E. Vargas, both of Miami; Stuart D. Wills, Cooper City, all of Fla.

[73] Assignee: Coulter Corporation, Hialeah, Fla.

[21] Appl. No.: 626,931

[22] Filed: Dec. 13, 1990

[51] Int. Cl.⁵ .................................................. G01N 1/10
[52] U.S. Cl. ........................................ 436/180; 436/174; 422/100
[58] Field of Search ................. 436/180, 174; 422/100; 73/864.83, 864.84

[56] References Cited

U.S. PATENT DOCUMENTS

| | | | |
|---|---|---|---|
| 3,600,953 | 8/1971 | Isreeli et al. | 422/82 |
| 3,759,667 | 9/1973 | Bannister et al. | 422/67 |
| 3,874,850 | 4/1975 | Sorensen et al. | 436/163 |
| 3,929,413 | 12/1975 | Young et al. | 436/53 |
| 4,253,846 | 3/1981 | Smythe et al. | 422/82 |
| 4,517,302 | 5/1985 | Saros | 422/100 |
| 4,526,754 | 7/1985 | Burn et al. | 422/82 |
| 4,640,821 | 2/1987 | Mody et al. | 436/52 |
| 4,680,270 | 7/1987 | Mitsumaki et al. | 436/52 |
| 4,691,580 | 9/1987 | Fosslien | 422/103 |
| 4,774,055 | 9/1988 | Wakatake et al. | 436/807 |
| 4,853,336 | 8/1989 | Saros et al. | 422/81 |

*Primary Examiner*—David L. Lacey
*Assistant Examiner*—Thomas E. Daley
*Attorney, Agent, or Firm*—Sidney N. Fox; Gerald R. Hibnick

[57] ABSTRACT

For use in automated or semi-automated hematology analysis apparatus, a method of introducing a volume of blood from a source thereof along a conduit leading to a sampling, metering and transfer valve assembly of the apparatus comprising the steps of drawing a predetermined volume of blood sample from the source, causing the drawn blood sample to travel along the conduit toward the valve assembly, providing detectors adjacent the inlet and outlet of the valve assembly and using vacuum to position the drawn blood sample so that it passes through the valve assembly and is disposed in metering condition within the valve assembly, the positioning being responsive to signals provided by the detectors.

32 Claims, 3 Drawing Sheets

ASPIRATION METHOD FOR HEMATOLOGY ANALYZING APPARATUS

CROSS REFERENCE TO RELATED PATENTS

The subject matter of each of the following patents is hereby incorporated by reference hereto as a part of this application for the disclosure contained therein:

U.S. Pat. No. 4,609,017 granted on Sept. 2, 1986 to Wallace H. Coulter et al. for Method and Apparatus for Transporting Carriers of Sealed Sample Tubes and Mixing the Samples;

U.S. Pat. No. 4,752,690 granted on June 21, 1988 to Bobby D. James for Method and Apparatus for Detecting Incongruities, Such As Air Bubbles, in Fluid Material.

FIELD OF THE INVENTION

This invention relates generally to hematology analyzing apparatus and more particularly provides an improved method for introducing whole blood samples to such apparatus for analysis.

BACKGROUND OF THE INVENTION

Automated and semi-automated hematology analysis apparatus of the type employed for measuring a plurality of parameters of a whole blood sample have been in common use for many years. One of such systems is the subject of U.S. Pat. No. 3,549,994 and in using such systems, means have been provided for introducing whole blood samples into the system manually via an open-mouthed sample container which is held up to an aspirating tube or probe from which it is aspirated and thereby directed to a metering, transfer and delivery valve assembly of the type taught by U.S. Pat. No. 4,445,391. The said type of valve assembly meters the aspirated sample into precise volume aliquots and delivered with a predetermined volume of diluent to the testing means provided within the system.

Although numerous improvements have been made over the years to systems of the type concerned, for many years the method and means for introducing sample to the system have remained unchanged. Some advances have been made in sample handling such as taught in U.S. Pat. No. 4,609,017 in that sealed sample containers have been provided and handled by automatic and semiautomatic feed arrangements using holding racks and piercing needle means to combine sample mixing and aspiration enabling with a goal to minimize technician interaction and reducing the sample volume required. In such apparatus, the piercing needle is coupled by a fluid conduit line to the metering, transfer and delivery valve assembly. In some of these systems, the piercing needle means is required to be physically located within a very short distance from the valve assembly. In such systems, the aspirated blood volume is required to be large enough to fill the needle, the connecting fluid conduit and the valve assembly. This aspirated blood volume, of course is continuous along such route and hence is much greated than required to fill the valve assembly.

In respect of systems wherein manual aspiration means are provided, again the volume of aspirated blood sample is much larger than necessary to enable the valve assembly to provide the required aliquot portions. Conservation of sample has been and remains an important and as yet unrealized goal to the extent theoretically possible. Even where the sample aspiration probe is directly secured to the valve assembly, the volume aspirated into the probe has been far greater than the theoretical minimum, the excess passing through the valve assembly and to waste. Thus whether the aspiration station, whether it involves a piercing needle semi-automatic or automatic mode or a manual aspiration probe mode, is remote from the valve assembly or closely adjacent the valve assembly, the resultant aspirated sample volume is greater than actually required for the determinations sought to be obtained.

Another deterrent to the efficient aspiration of whole blood sample is the structural complexity required where the aspiration station and the valve assembly are positioned closely adjacent one another. If it were possible to obtain minimum volume units of sample at a location remote from the valve assembly and transport said units to the valve assembly with preservation of their integrity so that only the volume required to establish the necessary fluid body for segmentation within the valve assembly to provide the aliquot portions is drawn, the volume of blood sample to be aspirated would be manifestly reduced.

Thus it would be desirous to provide an blood sample aspiration method which would enable the reduction of the volume of whole blood sample aspirated to an amount at least close to the theoretical minimum required to isolate the required aliquot portions of the sample necessary to obtain the desired parameters of said sample. Also sought is a method for locating the aspiration station remote from the valve assembly yet assuring continuity of sample and maintaining the integrity thereof. Further, another advantage sought is an inexpensive method to position the body of blood sample so that it just fills the flow path therefor within the sampling valve assembly. The method sought by the art to solve the above problems likewise should improve the ease of cleaning the aspiration lines from the probe tip through the blood sampling valve without needing the backflushing conventionally available.

SUMMARY OF THE INVENTION

The herein describe invention provides a method for introducing a volume of whole blood sample from a source thereof, either via piercing needle means or manual probe means, to a blood metering, transfer and delivery valve assembly, which volume is substantially equal to substantially the minimum volume required to establish a segmentable body of said sample within the valve assembly; driving the drawn volume of blood sample as a unit to and through the valve assembly to reach a location exterior of the valve assembly yet adjacent the sample outlet thereof; detecting the arrival of the leading edge of the drawn sample volume to a first location closely spaced from the entry port of the valve assembly; detecting the arrival of said sample volume to a second location closely adjacent the sample outlet of the valve assembly; and stopping the flow of said drawn sample volume at said second location to position said unit volume relative said valve assembly to permit the required segmentation of said drawn sample unit into aliquot portions thereof. Provision is made to effect backwash of the remainent sample volume by flowing diluent or rinse fluid to retrace the aspiration flow path.

DESCRIPTION OF PREFERRED EMBODIMENTS

Briefly, the aspiration method according to the invention herein consists of aspirating a volume of whole blood sample only sufficient to fill the interior sample aspiration flow path within the metering, transfer and delivery valve assembly of the hematology analyzing system, causing said volume to flow as a unit along a fluid conduit leading to the sample inlet of the metering, transfer and delivery valve assembly, through the interior sample aspiration flow path within the valve assembly and continuing from the outlet of said flow path through a fluid conduit exterior of the said valve assembly, there being an interface between the unit and a pilot fluid, detecting the arrival of the interface at a first location adjacent the sample inlet of the valve assembly to generate a first signal, detecting the arrival of the interface at a second location adjacent the sample outlet of the valve assembly, stopping the flow of said sample unit, using the first signal to initate the flow of said sample unit into the inlet port of the valve assembly, using the second signal to stop the flow of said sample unit at the second location, positioning the sample unit to permit operation of the valve assembly to segment the necessary aliquot portions as required, by operation of said valve assembly to segment said sample unit as required to obtain the desired parameters of said blood sample, the aspiration flow continues so that the interface is detected, the first signal causing the aspiration to cease and vacuum to continue the flow through the valve assembly to the second location, the second signal causing the flow to stop at the second location.

In the preferred embodiment detection of the blood sample unit by both detectors is required to effect stopping the flow of said travelling blood sample unit so that it is properly positioned relative to the metering, transfer and delivery valve assembly. The valve assembly then is operated to cause the segmentation of the sample unit to form the necessary sample aliquots. The valve assembly then is operated to deliver the aliquots with respective predetermined volumes of diluent, to the testing chambers of the system. The valve assembly then is operated to place the valve in backwash condition, whereupon vacuum is applied to direct any residual blood sample contained in the aspiration flow path through the fluid conduit and valve assembly to a waste chamber. Reverse flow of rinse or diluent liquid is initated to backwash said flow path readying the system for the next sample aspiration.

It is necessary that the fluid conduit be formed of a material to which the blood is non-adherent, such as for example, Teflon (a trademark of DuPont Co.), so that the blood does not adhere to the inner wall of said conduit. The pilot fluid preferably is isotonic diluent such as manufactured and sold by Coulter Electronics, Inc. under the registered trademark Isoton.

Figure 1:
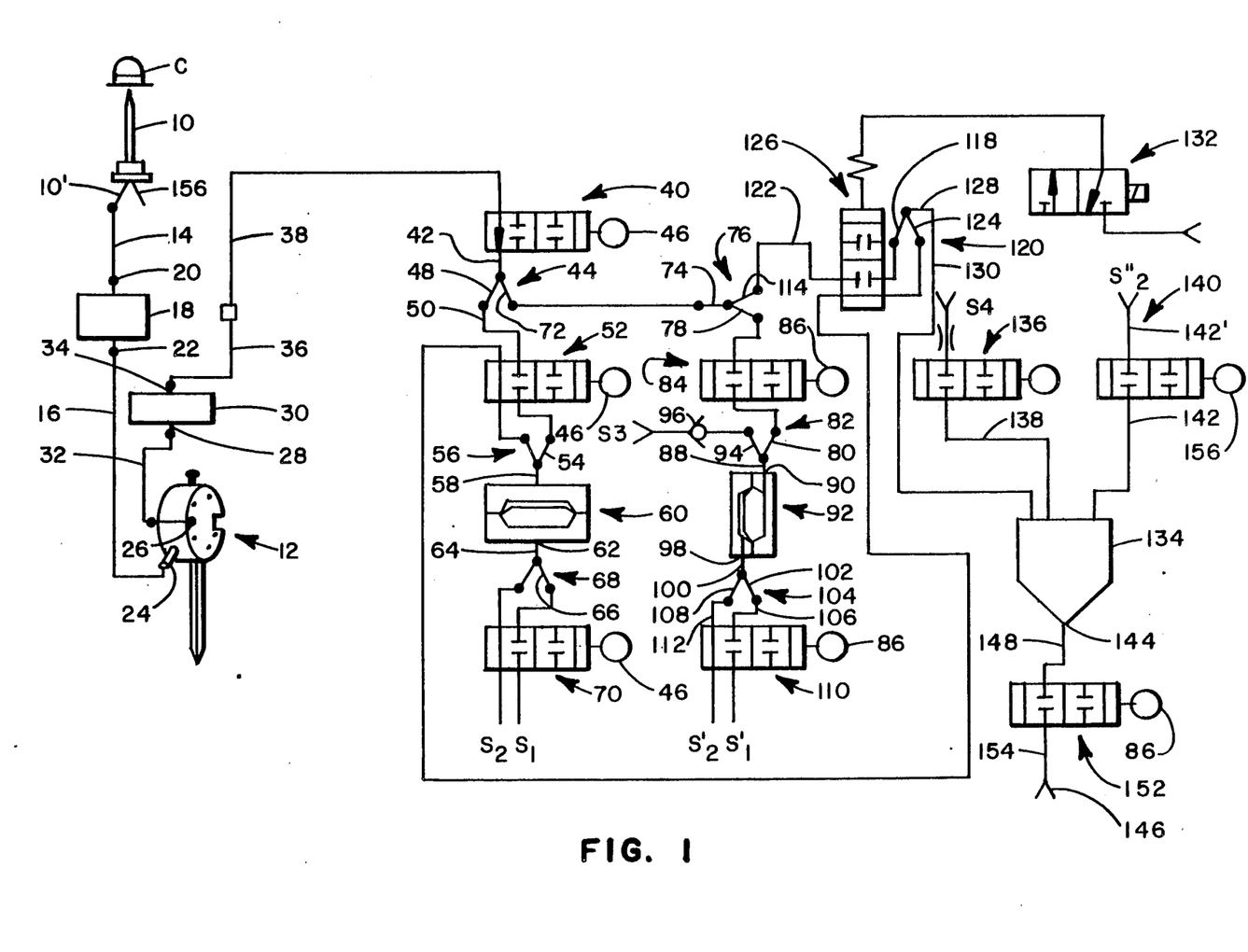
FIG. 1 is a schematic representation illustrating the aspiration method according to the invention.

Referring to FIG. 1 of the drawing, the aspiration station is represented by the piercing needle 10 which is coupled to the blood metering, transfer and delivery valve assembly 12 via first and second small bore flexible conduits 14 and 16 formed of Teflon material, with a first detector 18 interposed between said conduits. The piercing needle 10 is arranged to enter the sealed whole blood container C through the seal thereof. The outlet 10' of the piercing needle 10 is coupled to the conduit 14, thence to the input port 20 of the first optical detector 18. The outlet port 22 of the first optical detector 18 is positioned closely adjacent the sample inlet port 24 of the valve assembly 12 and coupled thereto by second flexible conduit 16. The sample outlet port 26 of the valve assembly 12 is coupled to the input port 28 of a second detector 30 by third flexible conduit 32, also formed of Teflon material. The outlet port 34 of the second detector 30 is coupled to fourth flexible conduit 36, in turn coupled through first pinch valve 40 to the leg 42 of first Y-connection 44, the first pinch valve 40 being controlled by solenoid 46. The arm 48 of first Y-connection 44 is coupled, via line 50 through second pinch valve 52 to the arm 54 of the second Y-connection 56, in turn coupled via leg 58 to the delivery side of first single stroke diaphragm pump 60, said diaphragm pump 60 having a predetermined volume, here 175 microliters. The input 62 of pump 60 is coupled to leg 64 of third Y-connection 68, the arm 66 of said third Y-connection 68 leading via third pinch valve 70 to a source S-1 of 30 PSI pressurized fluid.

Arm 72 of first Y-connection 44 is coupled to leg 74 of the fourth Y-connection 76. Arm 78 of fourth Y-connection 76 is coupled to arm 80 of the fifth Y-connection 82 through the fifth pinch valve 84. Fourth pinch valve 76 is controlled by solenoid valve 132. Arm 80 of the fifth Y-connection 82 is coupled via leg 88 of the fifth Y-connection 82 to the delivery port 90 of the second single stroke diaphragm pump 92. Arm 94 of the fifth Y-connection 82 is connected via check valve 96 to a source S-3 of isotonic diluent which serves as a pilot fluid in the system concerned herein. The second single stroke diaphragm pump 92 has a capacity of 1 cc. The input port 98 of pump 92 is coupled to the leg 100 and thence to arm 102 through the sixth pinch valve 110 via line 106 to the source S-1 of 30 PSI pressurized fluid, said sixth pinch valve 110 also being operated by solenoid 86.

The arm 114 of fourth Y-connection 76 is coupled to the arm 118 of seventh Y-connection 120 via line 122 passing through the fourth pinch valve 126. The fourth pinch valve 132 is controlled by solenoid valve 132. The leg 128 of seventh-Y connection 120 is coupled to the vacuum/waste chamber 134 via line 130. The vacuum/waste chamber 134 is coupled to source S-4 of 5 PSI pressurized fluid through seventh pinch valve 136 via line 138. The vacuum/waste chamber 134 is coupled to a vacuum source S-2" through eighth pinch valve 140 via lines 142 and 142', said eighth pinch valve 140 being controlled by solenoid 156. The outlet 144 of the vacuum/waste chamber 134 is coupled to a waste receptacle 146 along line 148 through ninth pinch valve 152 and line 154. Ninth pinch valve 152 is operated also by solenoid 86.

The preferred inner diameter of conduits 14, 16, 32 and 36 are identical, preferably 0.028 inches. In a preferred embodiment, the length of conduit 14 is 15.5 inches; the length of conduit 16 is 3.25 inches; the length of conduit 32 is 3.00 inches; the length of conduit 36 is 6.5 inches and the length of conduit 38 is 13.0 inches. The inner diameter of conduit 38 preferably is 0.040 inches, hence larger than the inner diameter of the conduits 14, 16, 32 and 36.

Figure 3:
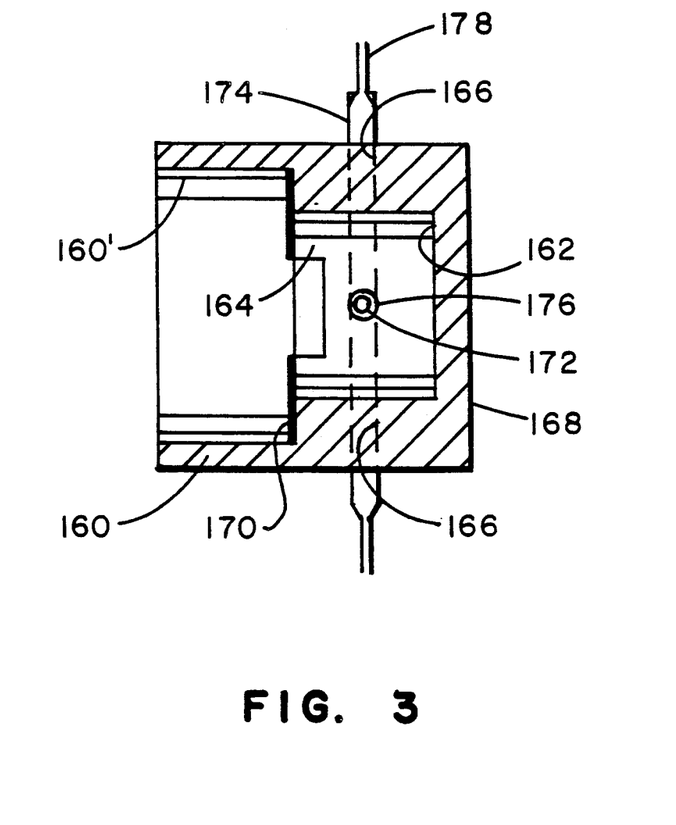

Preferably, the optical detectors 18 and 30 are identical to the detectors described and claimed in U.S. Pat. No. 4,752,690 of June 21, 1988 incorporated by reference herein. The preferred detectors 18 and 30 provide electrical signals indicative of optical opacity of the fluid flowing therethrough. The signals thus derived are compared against a diluent reference level signal to provide a resulting signal output indicating the presence of the interface of the flowing blood sample unit. Each said detector is adapted to detect changes in fluid density, i.e. opacity, of the fluids flowing therethrough. This requires that the detector units respond to subtle changes in light level. The detector is constructed to be free from extraneous surrounding or reflecting light. A rigid block 160 of material (substantially impervious to the passage of light therethrough) is bored, machined, cast, molded or otherwise formed to provide a fairly deep, well-like central opening 160' therein from which two substantially parallel additional lozenge shaped, receptacle-like openings 162 (only one illustrated) extend downwardly well into the body of block 160. A vertical wall member 164, separating the two parallel openings 162 is provided as a result of the casting or drilling operation.

Horizontal through holes 166 are formed through opposite sides of the block 160 approximately midway between its bottom 168 and top 170 of the openings 162. A second horizontal through hole 172 extends into and through block perpendicular to the holes 166. A stainless steel tube press-fitted into and through the holes 172 providing a rigid attachment fitting extending from both sides of the block. Utilizing the manufacturing holes for drill access, a window 176 is defined of relatively small diameter (0.19 inches) which is drilled through the central wall member 164 and through the stainless steel tube 174. A close fitting length of transparent rigid material 178 is inserted into and through the stainless steel tube 174 and is secured to it with suitable bonding material.

The light sensing assembly is accuratedly oriented within the block 160 so that the axial centers thereof are aligned with the center of the window 176 thus assuring that the light will pass through the window with minimum loss due to the tolerance of the associated parts of the assembly. The detector 18 senses and causes a signal to be generated which is transmitted to means for operating the solenoid controlled pinch valves which in turn control flow of the blood sample unit along the flow path concerned. For more details concerning the construction and operation of the detectors 18 and 30, reference is made to U.S. Pat. No. 4,752,690 incorporated by reference herein.

According to the method of the invention, prior to the initiation of the aspiration of a whole blood sample, the entire aspiration system, including the valve assembly 12 and the respective conduits have been backwashed and filled with the isotonic diluent, the latter functioning as the pilot fluid during the transport of the aspirated sample. Now the solenoid 46 is activated, which causes the pinch valve 40 to operate, to unpinch the line 38 leading to the leg 42. This creates the air bubble which serves as the interface for the leading end of the aspirated whole blood sample. Solenoid 46 also activates pinch valve 52 after the piercing needle 10 passes through the seal of container C to reach the whole blood sample therein. With the solenoid 46 still activated, both pinch valve 52 and 70 unpinch. This activates the diaphragm pump 60, drawing the volume of whole blood sample, referred to as the blood sample unit, into the flexible conduit 14. The blood sample unit as it travels along conduit 14 may or need not reach the input port 20 of the first detector 18. However, it will not reach the sample input port 24 of the sampling, metering and transfer valve 12.

When the air bubble (sample/pilot fluid interface) reaches the sensing means within the detector 18, a signal is generated and a command issued from the control means (not shown). The solenoid 70 is deactivated and pinch valves 126 and 140 are activated, with pinch valve 40 still in the unpinching condition. Vacuum thus is applied to the conduit lines 38, 36, 32, 16 and 14, causing the travel of the blood sample unit along said conduits past the first detector, into the valve assembly (then in loading condition) and passes through the sample outlet 28 of the valve assembly 12 along conduit 32 to the detector 30. When the air bubble at the leading edge of the sample unit is detected by the second detector 30, and while the first detector still generates the signal indicating that the length of the sample unit is still within the first detector, a command is directed to the solenoid 46 to deactivate the pinch valve 40, whereupon the pinch valve pinches the line 38, 42, stopping the blood sample unit.

Now the valve assembly 12 is operated to segment the body of blood sample within the interior loading flow path therein, whereby to isolate the required aliquot portions thereof. Diluent is fed to the valve assembly driving the respective aliquot portions with given volume of diluent respectively to the mixing and testing baths provided in the analysis system whereby the testing is performed to provide the desired parameters of said sample. The pinch valves 40, 126 and 86 are caused to operate to unpinch the respective lines passing therethrough whereby vacuum is drawn on the conduit 138 causing the remanent blood sample to be drawn to the vacuum/waste chamber 134 and, through line 154 to the waste reservoir (container) 146.

Figure 2:
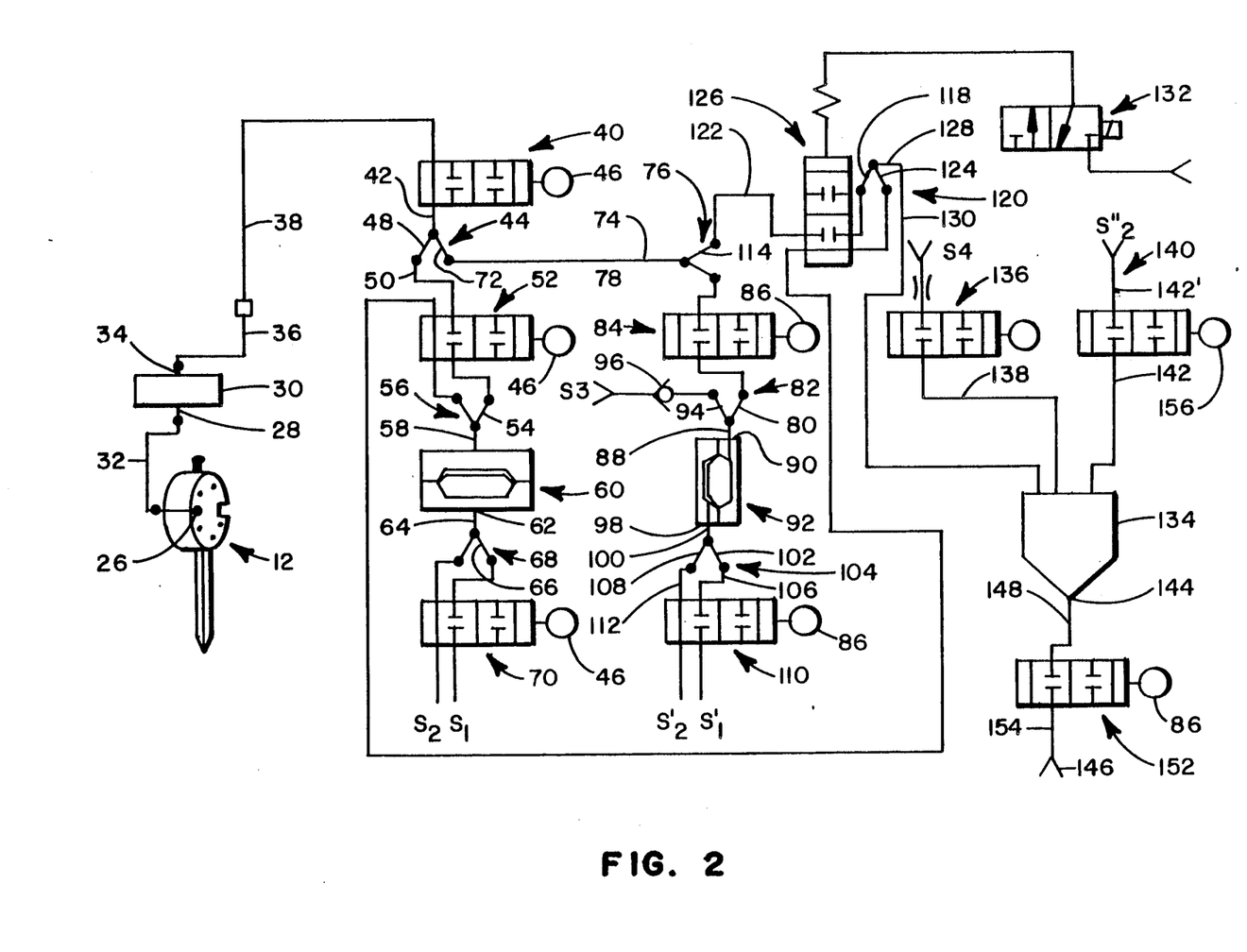
FIG. 2 is a schematic representation illustrating a modification of the aspiration method according to the invention; and, FIG. 3 is an elevational sectional view of a detector employed in practising the aspiration method according to the invention.

Referring to FIG. 2, the manual mode of the method according to the herein invention shall be described. The volume of sample required is reduced compared to the volume required employing the automatic (piercing needle, etc) mode since the volume needed to fill conduits 14 and 16 is not required. The sample probe 136 is secured to the sampling, metering and transfer valve assembly 12 with the sample outlet thereof coupled to conduit 32. Only a single detector 30 on the outlet side of the valve assembly 12 is required. The input of the aspiration probe 136, which had been filled with pilot fluid also has an inwardly arced meniscus so that the air bubble is created upon entry of the blood sample into the probe 136 when aspiration is initiated. The said air bubble defines the leading edge of the body of blood sample as it travels up the probe and into the valve assembly (which is disposed in the loading condition thereof).

When the air bubble reaches the sensing means of the detector 30, a signal is generated and directed to the control means for system and the pinch valves 52 and 70 operate to pinch the aspiration lines, also causing the pinch valve 40 to pinch line 38 and stop the travel of the sample unit. The valve assembly 12 is operated to segment the sample unit within the valve assembly and thus provide the necessary aliquot portions. Diluent is introduced to flush the aliquots, along with the diluent, to the mixing vessels and testing vessels of the analysis system.

The purpose of the detectors according to the invention is to position the blood sample unit so that its length is close to the minimum necessary to provide the number of sample aliquots required for determining the parameters desired and, further, to control the flow of the blood sample unit.

It should be noted that the conduits, pinch valves, valve assembly and probe can be backwashed using the second diaphragm pump to provide a reverse flow along the aspiration route, subsequent to the completion of the discharge of the remainent portions of the sample unit to the waste receptacle 146. One also can wash the system by drawing diluent (or rinsing liquid) by aspirating same or using the line 156 to introduce said diluent under the reduced pressure (5 PSI) unpinching pinch valve 136.

It is clear that one skilled in the art can make changes and/or modifications to the method of the invention yet remain within the scope of the invention as claimed hereinafter.

We claim:

1. A method of introducing a whole blood sample from a source thereof into a blood analyzing system which includes an aspirator probe; a blood sampling, metering and transfer valve assembly operating between a loading condition and a delivery condition; said valve assembly having a sample inlet port, a sample outlet port and an internal continuous passage therebetween and, in the loading condition, defining a continuous sample flow path therebetween extending from the inlet port to the outlet port thereof; said valve assembly capable of being operated to assume the delivery condition from the loading condition thereby segmenting a body of blood sample into at least one precise volume aliquot portion thereof for delivery to the blood analyzing system; small bore conduit means coupled between the aspirator probe and the inlet port and to the outlet port leading downstream therefrom; aspirator pump means for drawing the blood sample into the probe, the blood sample having leading and trailing ends; a source of vacuum and detector means arranged proximate to said conduit means at least at a first location downstream of but adjacent the outlet port of the valve assembly for monitoring the passage of fluid along the conduit means and sensing the arrival of the leading end of the blood sample at the first location; the method comprising the steps of drawing a predetermined volume of a blood sample as a unit into the aspirator probe; causing the blood sample unit to travel along the conduit means; stopping the aspirator pump means; using vacuum from said source continue the travel of the blood sample unit; detecting the arrival of the leading end of the blood sample unit at the first location by said detecting means; stopping the travel of the blood sample unit at the first location; operating the valve assembly to change the condition thereof from the loading condition to the delivery condition whereby to segment the blood sample unit into aliquots of a predetermined volume and deliver an aliquot to a mixing and testing location of the blood analyzing system; returning the valve assembly to the loading condition; and thereafter resuming the travel of any remainent portion of the blood sample unit.

2. The method as claimed in claim 1 in which said detector means comprise at least one optical detector.

3. The method as claimed in claim 1 in which the detector means comprise first and second detectors, the first detector arranged proximate the conduit at said first location and the second detector arranged proximate the conduit means at a second location adjacent the inlet port of the valve assembly so as to detect the arrival of the leading end of the blood sample unit at said second location and generate a signal; applying said vacuum to said conduit means in response to said signal causing the blood sample unit to continue its travel along said conduit means and pass through the valve assembly; said detector means comprise optical detectors which stop the travel of said blood sample unit when the signals from said optical detectors indicate the presence of the trailing end of said blood sample unit at the second location and subsequently the arrival of the leading end of the blood sample unit at the first location.

4. The method as claimed in any one of claims 1, 2 or 3 further including the step of introducing an air bubble at the leading end of the blood sample unit during the initiation of the drawing thereof from said source and the air bubble is detected by the detector means.

5. The method as claimed in any one of claims 1, 2 or 3 further including the step of initially filling the aspirator probe, the conduit means and the continuous flow path when the valve assembly is in the loading condition with a pilot fluid before drawing the sample unit into the aspirator probe to define an interface between the leading end of the blood sample unit and the pilot fluid, the interface being detected by the detector means.

6. The method as claimed in any one of claims 1, 2 or 3 in which the drawing step is carried out by use of a single stroke diaphragm pump.

7. The method as claimed in any one of claims 1, 2 or 3 wherein the aspirator probe comprises a piercing needle, the sample source being a sealed container; piercing the sealed container with the piercing needle and employing a single stroke diaphragm pump so as to draw the blood sample unit into the piercing needle.

8. A method for introducing a whole blood sample from a source thereof into a blood analyzing system of the type which includes aspirator probe means, a blood sampling, metering and transfer valve assembly having a sample inlet and a sample outlet, conduit means coupled between the sample inlet and the aspirator probe means and to the sample outlet, an internal passage within the valve assembly constructed so as to define a flow path for a continuous blood sample unit, the valve assembly operating between a loading condition and a delivery condition, the flow path being defined when the valve assembly is in the loading condition, the valve assembly being operated to assume the delivery condition thereby segmenting the blood sample unit to define a precise volume aliquot thereof and delivery of said aliquot to an exterior location within the blood analyzing system for mixing and testing, an aspirator pump capable of drawing the blood sample unit of predetermined volume into the aspirator probe means, a source of less than atmospheric fluid pressure and detector means including first and second detectors positioned adjacent the valve assembly for monitoring the passage of liquid through the conduit means and flow path and generating a signal in response thereto and flow control means; said method comprising the steps of:

positioning the first detector proximate the conduit means at a first location adjacent the sample inlet;
employing the aspirator pump to draw a predetermined volume blood sample unit into the aspirator probe means and conduit means thereby creating a blood sample unit with leading and trailing ends;

sensing the arrival of the leading end of the blood
sample unit at the first location by said first detector and generating a signal in response thereto;

stopping the travel of the blood sample unit in response to the signal from the first detector when the leading end thereof is sensed;

stopping the drawing of the blood sample unit and applying less than atmospheric fluid pressure from said source to cause the blood sample unit to continue to travel along the conduit means and pass through the inlet of the valve assembly along the sample flow path;

continuing the application of less than atmospheric fluid pressure to effect continued travel of the blood sample unit through the outlet of the valve assembly to a second location downstream thereof;

positioning the second detector proximate the conduit means at a second location downstream of the outlet of the valve assembly but adjacent thereto;

sensing the arrival of the leading end of the blood sample unit at said second location by said second detector and generating a signal in response thereto;

stopping the continued travel of said blood sample unit at said second location by discontinuing the application of the less than atmospheric fluid pressure to the conduit means in responsive to said signal provided by said second detector;

operating the valve assembly to change the condition thereof from the loading condition to the delivery condition when the travel of the blood sample unit is stopped whereby to segment the blood sample unit within the valve assembly so as to create an aliquot portion of precise volume of said blood sample unit and deliver the said aliquot portion to a mixing and testing location within the blood analyzing system; and, thereafter, returning the valve assembly to the loading condition.

9. The method as claimed in claim 8 in which the entire flow path, including the aspirator probe means, the conduit means and the valve assembly, which includes the internal sample passage thereof, is filled with a pilot fluid prior to drawing of the blood sample unit into the aspirator probe means whereby to define an interface between the leading end of the drawn blood sample unit and said pilot fluid.

10. The method as claimed in claim 8 including a source of diluent; and the step of reversing the flow within the conduit means and associated continuous flow path, after the valve assembly has been returned to the loading condition and prior to drawing of a followed blood sample unit, by introducing the diluent from said source to the conduit means downstream of the outlet whereby to backwash the entire flow path including the aspiration probe means.

11. The method as claimed in any one of claims 1, 2 or 3 in which the conduit means are constructed from a flexible fluoroethylene derivative material non-adherent to blood and the flow control means comprise plural pinch valves.

12. In a method for introducing a volume of blood from a source thereof via sample receptor means to a blood sampling, metering and transfer valve assembly of a blood analyzing system in which the valve assembly is constructed so as to operate between a loading condition and a delivery condition and has sample inlet and outlet ports and a conduit portion constructed of a non-blood adhering material and coupled to the sample receptor means and the inlet and outlet ports thereby defining a continuous sample flow path from the sample receptor means through the valve assembly and downstream of the outlet port; the method including the steps of drawing a predetermined volume of blood sample as a unit from the source thereof into the sample receptor means, defining a sample body unit of a blood sample along said conduit portion coupled to the inlet port of the valve assembly, the body unit of blood sample having leading and trailing ends, establishing a source of reduced pressure and coupling the source of reduced pressure to the valve assembly via the conduit portion coupled to the outlet port of the valve assembly; the improvement further comprising the additional steps of establishing a continuous body of pilot fluid along the flow path from the sample source including the sample receptor means, the conduit portion, the inlet and outlet ports of the valve assembly and the internal passage constructed so as to individually link said ports at a time prior to the drawing of the body unit of blood sample for creating an interface between the body of pilot fluid and the body unit of blood sample after drawing of the body unit of blood sample; sensing the leading end of the body unit of blood sample at a first location along the conduit portion short of the inlet port of the valve assembly and providing a first signal, stopping the travel of the body unit of blood sample in response to said first signal before the body unit of blood sample reaches the inlet port, applying reduced pressure from said source to the conduit coupled to the outlet port of the valve assembly to continue the travel of the body unit of blood sample through the valve assembly along the internal passage therein through the outlet port and to a second location downstream thereof, sensing the arrival of the leading end of the body unit of blood sample at said second location and providing a second signal, sensing the presence of the trailing end of the body unit of blood sample at said first location, and subsequently stopping the travel of the body unit of blood sample at said second location only if the presence of the trailing end of the body unit of blood sample is indicated when the second signal is provided.

13. The method as claimed in claim 12 further including the steps of operating the valve assembly to segment the body unit of blood sample within the valve assembly to define an aliquot portion thereof and deliver said aliquot portion to a predetermined location within the blood analyzing system at a time subsequent to the provision of the second signal and the stopping of the travel of said body unit of blood sample in response thereto, and, thereafter, returning the valve assembly to its loading condition and directing the remaining blood of the body unit of blood sample to a predetermined location at a time subsequent to the completion of the segmentation and the delivery of the aliquot portion.

14. The method as claimed in claims 12 or 13 in which an air bubble is formed at the interface between the body unit of blood sample and the pilot fluid to denote said interface, the air bubble being sensed to generate the respective signals.

15. The method as claimed in claim 12 or 13 further including the step of pinching the conduit just prior to drawing of the blood whereby an air bubble is introduced at the leading end of the body unit of blood sample to denote the interface between the body unit of blood sample and the pilot fluid.

16. The method as claimed in claim 13 further comprising the step of backflushing the flow path along the conduit portions and valve assembly using pressurized fluid directed in a reverse direction relative the flow of blood during the step of drawing the blood, said backflushing being undertaken subsequent to said returning of the valve assembly to its loading condition.

17. The method as claimed in claims 12 or 13 in which the pilot fluid is an isotonic diluent.

18. The method as claimed in claims 12 or 13 wherein the volume drawn is only slightly greater than the minimum volume required within the valve assembly for disposition thereof for the delivery condition.

19. The method as claimed in claims 12 or 13 in which the flow control means comprise pinch valves.

20. The method as claimed in claims 13 or 14 in which the flow control means comprise solenoid operated pinch valves.

21. A method of introducing a predetermined volume unit of a sample from a source thereof into a metering and transfer valve assembly of an analyzing system in which there is a source of reduced pressure, an aspirator probe, the metering and transfer valve assembly constructed so as to operate between a loading condition and a delivery condition and having a sample inlet, port a sample outlet port, a continuous internal passage defined within the valve assembly between the sample inlet and outlet ports during the loading condition and a flexible conduit means constructed so as to define with said internal passage a continuous flow path from the aspirator probe to and through the valve assembly at least downstream of the outlet port', the conduit means including a first flexible conduit constructed so as to link the aspirator probe to the inlet port and coupled thereto and a second flexible conduit coupled to the outlet port', signal generating detector means arranged proximate to the first and second conduits at first and second locations respectively adjacent the inlet and outlet ports so as to monitor the passage of fluid along the flow path; aspirator pump means coupled to the second conduit for drawing a predetermined volume unit of sample from the source thereof into the aspirator probe and the first conduit, the volume unit having a leading end and a trailing end; flow control means responding to the detector signals and operating upon the flow of the sample unit along the flow path; the method comprising the steps of:
   causing the aspirator pump means to draw a predetermined volume of sample as a unit into the aspiration probe and along the flow path;
   detecting from a first detector of said detecting means the arrival of the leading end of said sample unit at a first location short of the inlet port and generating a first signal in response thereto;
   stopping the aspirator pump means;
   stopping the flow of the said volume unit at said first location along the flow path in response to said first signal from said first detector;
   applying reduced pressure to the second conduit to resume the flow of said volume unit along the flow path and through the inlet port, the internal passage and the outlet port of the valve assembly and into the second conduit downstream of the outlet port;
   detecting from a second detector of said detecting means the arrival of the leading end of said volume unit at the second location and generating a second signal in response thereto; and,
   stopping the flow of said volume unit at the second location in response to said second signal only if the trailing end of said volume unit is sensed at the first detector indicating its presence at the first location.

22. The method according to claim 21 in which said first and second locations are adjacent the respective inlet port and outlet port.

23. The method according to claim 21 and the additional step of:
   initially filling the continuous flow path with a pilot fluid before drawing the unit of sample into the aspirator probe whereby creating a detectable interface between the pilot fluid and the leading end of said sample unit.

24. The method according to claim 21 in which a meniscus is permitted to be present at the entry to the aspirator probe prior to drawing of the predetermined volume unit of sample thereinto so that an air bubble is drawn into the aspirator probe at the leading end of said volume unit when said volume unit is drawn into the aspirator probe, the air bubble denoting the interface.

25. The method according to any one of claims 21, 22 or 23 in which the flow control means comprise pinch valves.

26. The method according to any one of claims any one of claims 21, 22 or 23 in which the volume of the sample unit drawn into the aspirator probe is only slightly greater than the minimum volume required to fill the path defined by the inlet port, the internal passage and the outlet port of the valve assembly.

27. The method according to any one of claims 21, 22 or 23 in which only reduced pressure is employed to effect flow of said volume unit subsequent to the stopping of the travel of said volume unit at the first location.

28. A method of introducing a predetermined volume unit of whole blood sample from a source thereof into a blood analyzing system which includes a source of vacuum, a metering and transfer valve assembly constructed so as to operate between a loading and a delivery condition and having sample inlet and sample outlet ports, a continuous internal passage between the inlet and outlet ports and conduit means constructed so as to define with said internal passage during the loading condition a continuous flow path from an aspirator probe to and through the valve assembly at least downstream of the outlet port; the conduit means including a first conduit constructed so as to link the aspirator probe to the inlet port and a second conduit coupled to the outlet port; signal generating detector means positioned adjacent to the inlet and outlet ports for monitoring the passage of fluid along the flow path; aspirator pump means coupled to the second conduit for drawing a predetermined volume unit of sample from the source thereof into the aspirator probe and the flow path along the first conduit, the volume unit having a leading end and a trailing end; flow control means responding to the detector signals and operating upon the flow of the volume unit along the flow path; the method comprising the steps of:
   employing the aspirator pump means to draw a predetermined volume unit of the blood sample into the aspiration probe and along the flow path;
   stopping the aspirator pump means upon completion of the drawing of the predetermined volume of the blood sample unit;

continuing the flow of the blood sample unit along the flow path;

detecting by said detecting means arrival of the leading end of the blood sample unit at the first location and generating a signal in response thereto;

stopping the flow of the blood sample unit at the first location in response to said signal;

applying a vacuum from said source to the second conduit to continue the flow of the blood sample unit along the flow path through the inlet port, the internal passageway, the outlet port and second conduit;

sensing the position of the blood sample unit relative to the first and second locations and generating a second signal when the leading end of the blood sample unit reaches the second location and the trailing end of the blood sample unit is sensed as present at the first location;

stopping the flow of the blood sample unit at the second location in response to said second signal;

operating the valve assembly to segment the blood sample unit within the valve assembly whereby to isolate an aliquot of precise volume of said blood sample unit within the valve assembly;

delivering the isolated aliquot from said valve assembly to a predetermined location within the blood analyzing system; and returning the valve assembly to its loading condition.

29. The method according to claim 28 and the additional step of:

initially filling the continuous flow path with a pilot fluid before drawing the blood sample unit into the aspirator probe and creating an interface between the leading end of the blood sample unit and the pilot fluid when the blood sample unit is drawn.

30. The method according to claims 28 or 29 further including the steps of applying said vacuum from the vacuum source to the flow path diverting any remainent sample unit after the delivery to a waste receptacle subsequent to return of the valve assembly to its loading condition.

31. The method according to claims 28 or 29 wherein the pump means comprise a single stroke pump operative to draw the predetermined volume to define the blood sample unit into the aspirator probe whereby limiting the volume drawn to the quantity required to fill the flow path between the entry to the sample flow path and the outlet of the sample flow path of the valve assembly.

32. The method according to claims 28 or 29 in which the conduit means are constructed from a flexible material and the flow control means are pinch valves positioned along the conduit means, the pinch valves being operated selectively to permit and to stop liquid flow along the flow path defined by the conduit means.

* * * * *